United States Patent
Pressman et al.

(10) Patent No.: US 9,586,814 B2
(45) Date of Patent: Mar. 7, 2017

(54) SOLID STATE AMPEROMETRIC CHLORAMINE SENSOR

(71) Applicant: The United States of America as Represented by the Administrator of the U.S. Environmental Protection Agency, Washington, DC (US)

(72) Inventors: Jonathan G. Pressman, Cincinnati, OH (US); Woo Hyoung Lee, Orlando, FL (US); David G. Wahman, Cincinnati, OH (US)

(73) Assignee: The United States of America as represented by the Administrator of the Environmental Protection Agency, Washington, DC (US)

( * ) Notice: Subject to any disclaimer, the term of this patent is extended or adjusted under 35 U.S.C. 154(b) by 239 days.

(21) Appl. No.: 13/939,959

(22) Filed: Jul. 11, 2013

(65) Prior Publication Data
US 2015/0014165 A1    Jan. 15, 2015

(51) Int. Cl.
*G01N 27/26* (2006.01)
*B81B 1/00* (2006.01)
(Continued)

(52) U.S. Cl.
CPC ........... *B81B 7/02* (2013.01); *G01N 27/4045* (2013.01); *G01N 33/188* (2013.01)

(58) Field of Classification Search
CPC ...... G01N 27/404; G01N 27/42–27/44; G01N 27/48; G01N 27/49; G01N 27/304;
(Continued)

(56) References Cited

U.S. PATENT DOCUMENTS

| 7,087,150 | B2 | 8/2006 | Feng | |
|---|---|---|---|---|
| 2003/0205465 | A1* | 11/2003 | Feng | 204/415 |
| 2011/0042225 | A1* | 2/2011 | Adeloju | 205/170 |

FOREIGN PATENT DOCUMENTS

CA      2 482 011 A1    2/2004

OTHER PUBLICATIONS

"Anodic Voltammetric Determination of Monochloramine in Water", Davies, The University of Wisconsin Milwaukee, 1985.
(Continued)

*Primary Examiner* — Gurpreet Kaur (57) ABSTRACT

A monochloramine microsensor includes an elongated housing defining a central axis and an open interior and having a capillary opening at one end. A semi-permeable membrane covers the capillary opening, the semi-permeable membrane allowing diffusion of chloramines there-through while preventing water from entering into the interior of the housing. A chloramine sensitive element in the form of a wire, fiber or nanotube is mounted within the housing, the chloramine sensitive element, when used in conjunction with an anode, outputs current in an amount proportional to the concentration of chloramine present in a liquid sample in which the chloramine sensitive element is immersed. The chloramine sensitive element extends along a length of the central axis to a first end adjacent to and spaced from the semi-permeable membrane. The chloramine sensitive element is a gold wire, a platinum wire, a carbon fiber or a carbon nanotube.

20 Claims, 6 Drawing Sheets

(51) Int. Cl.
*B81B 7/02* (2006.01)
*G01N 27/404* (2006.01)
*G01N 33/18* (2006.01)

(58) Field of Classification Search
CPC ........ G01N 27/31; G01N 27/40; G01N 27/27;
G01N 27/4035; G01N 27/301; G01N
27/32; G01N 27/308
See application file for complete search history.

(56) References Cited

OTHER PUBLICATIONS

"Amperometric Determination of Hypochlorous Acid and Monochloramine at Gold Electrodes", Tsaousis, The University of Wisconsin Milwaukee, 1985.
"Electrochemical Behavior of Chloramines on the Rotating Platinum and Gold Electrodes", Piela et al., Journal of Electrochemical Society, 150 (5), Mar. 18, 2003.
"Free Chlorine and Monochloramine Application to Nitifying Biofilm: Comparison of Biofilm Penetration, Activity, and Viability", Lee et al., Enviromental Science & Technology, 2011.
"Characterization and Application of a Chlorine Microelectrode for Measuring Monochloramine Within a Biofilm", Lee et al., Sensors and Actuators B: Chemical, Jan. 25, 2010.

* cited by examiner

SOLID STATE AMPEROMETRIC CHLORAMINE SENSOR

BACKGROUND OF THE INVENTION

Field of the Invention

The present invention relates to an electrochemical quantitative analytic tool for in situ monitoring of monochloramine in aquatic systems and for measurement of monochloramine concentration profiles within biofilm for microscopic study of its kinetics.

The Prior Art

Monochloramine ($NH_2Cl$) has been used in low concentrations as a secondary disinfectant in treatment of municipal water supplies as an alternative to chlorination. Monochloramine is more stable and does not dissipate as rapidly as free chlorine. However, while the tendency of monochloramine to convert organic materials in the water to carcinogens, e.g., chloroform and carbon tetrachloride, is much lower than that of free chlorine, it remains a concern.

Many water utilities have switched from free chlorine to monochloramine as a secondary disinfectant to comply with disinfectant by-product (DBP) regulations because of the tendency of monochloramine to form lower levels of DBPs. A nitrification risk is associated with chloramine addition due to ammonia addition for chloramine formation and ammonia's subsequent release during chloramine decay. Nitrification in drinking water distribution systems may result in water quality degradation and non-compliance with existing regulations. It has been established that nitrifying biofilm is involved in nitrification episodes in water utilities. However, the present understanding of distribution system nitrification and its control is incomplete. In addition, microscopic biofilm research on disinfectant penetration and nitrification has been limited due to the lack of necessary tools. Microelectrode sensor techniques, e.g., the present invention, are required to profile chemical constituent transport and reaction and to monitor growth and inactivation, elucidating nitrification within distribution system biofilm. The ability to monitor at the microscopic level is in great demand in various research and development areas in biochemistry and environmental engineering. To evaluate nitrification and nitrifying biofilm control strategies in water utilities, information on disinfectant biofilm penetration and its effect on biofilm activity, viability, and recovery between monochloramine and free chlorine is required. A requirement met by the present invention.

Figure 5:
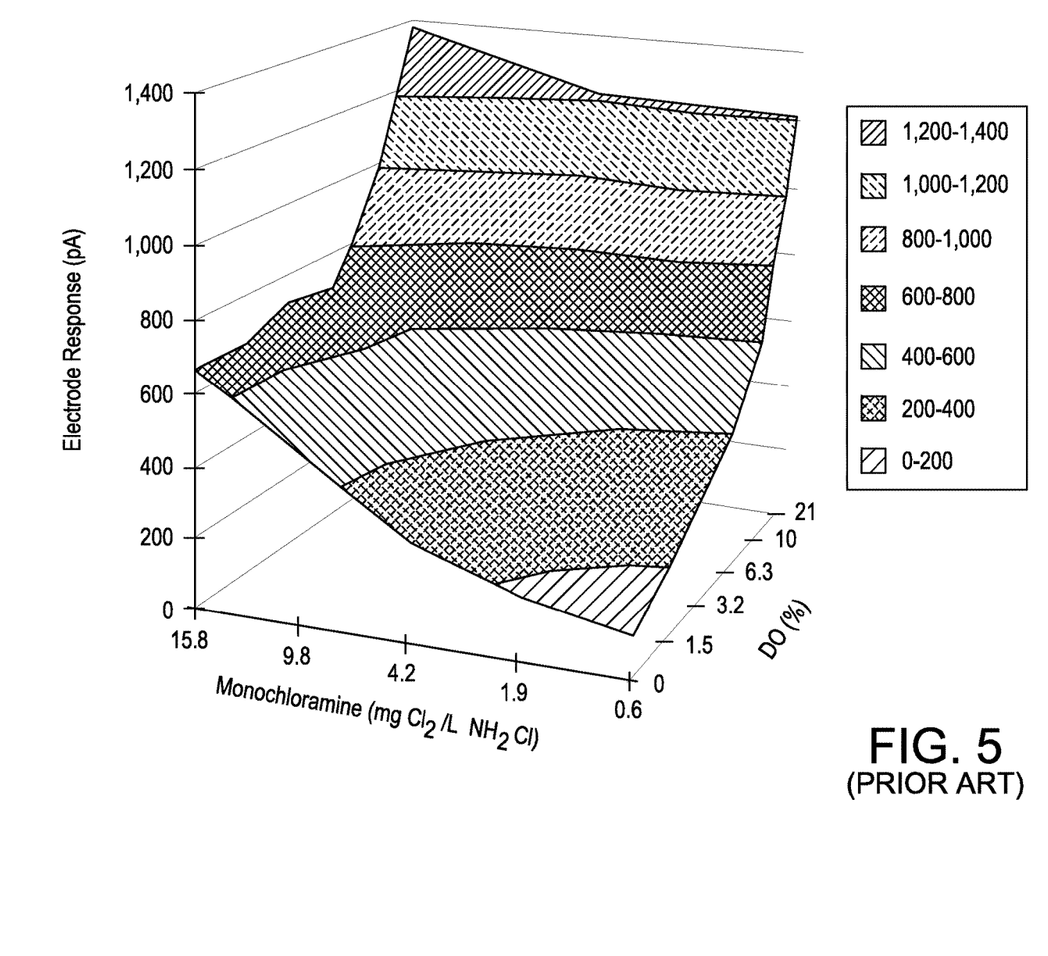
FIG. 5 shows a 3-D calibration curve for a modification of the chloramine sensor disclosed by W. H. Lee et al (2011) (prior art).
Figure 6:
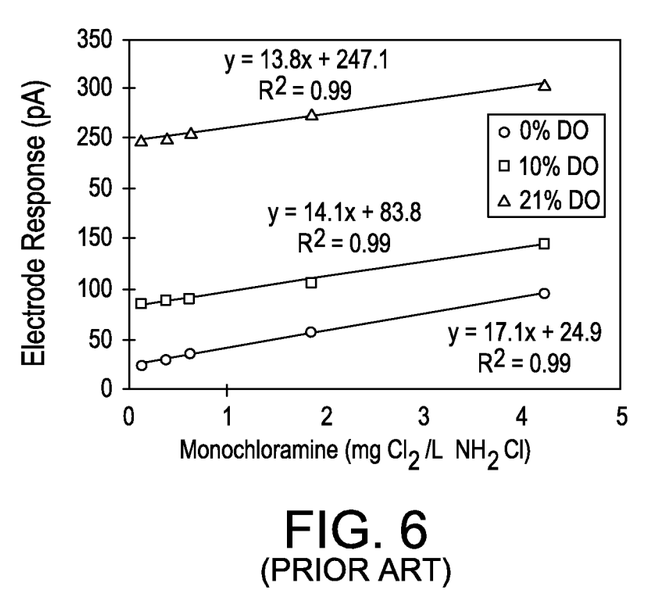
FIG. 6 shows multiple calibration curves of the chloramine sensor of W. H. Lee (2010) (prior art).

Several researchers have reported on electrochemical monochloramine sensors using a platinum or gold disk (or electrode) or platinum wire. Previous work using platinum microelectrodes showed dissolved oxygen (DO) interference during monochloramine measurement, resulting in generation of multiple calibration curves. For example, FIG. 5 shows a 3-D calibration curve for a modification of the chloramine sensor disclosed by W. H. Lee, D. G. Wahman, P. Bishop, and J. G. Pressman (2011) "Free chlorine and monochloramine application to nitrifying biofilm: comparison of biofilm penetration, activity, and viability." *Environmental Science and Technology*, 45, 1421-1419. FIG. 6 shows multiple calibration curves obtained using a modified version of the device of W. H. Lee, J. G. Pressman, D. G. Wahman, and P. L. Bishop (2010) "Characterization and application of a chlorine microelectrode for measuring monochloramine within a biofilm." *Sensors and Actuators B*," 145(2), 734-742, indicative of DO interference.

Chloramine amperometric sensors with a noble metal in non-compact form are disclosed in U.S. Pat. No. 7,087,150 and in Canadian Patent No. 2482011. The non-compact form may be a gas diffusion electrode, which can include metal mesh, carbon paper, carbon cloth, metal/carbon powder loaded on a porous membrane, or any combination thereof. However, such electrodes are too large, i.e., a 0.41 mm diameter platinum wire or gold mesh and a 25.1 mm overall diameter, to apply at the small scale (~10 microns) required for microscopic study, e.g., in situ monitoring of monochloramine biofilm penetration both spatially and temporally. Applicants know of no commercially available miniaturized needle type chloramine sensitive sensor. Further, conventional sensors limit the access of reduced chloramine species to the sensing electrode (cathode) due to the geometry of the sensing electrode; therefore, sensor linearity decreases at high chloramines concentrations, e.g. 2 mg $L^{-1}$. Another problem with currently available chloramine amperometric sensors is, as mentioned above, dissolved oxygen (DO) interference during monochloramine measurement. The present inventors have experienced dissolved oxygen interference during monochloramine measurement using a prior art platinum microelectrode, which required generation of a 3D surface calibration curve (response vs. DO vs. monochloramine concentration) or two calibration curves with different DO concentrations., e.g., 0% DO and 21% fully saturated DO, significantly limiting potential use of the microelectrode.

Relevant publications for understanding the present invention (e.g., sensor application to biofilm study and data interpretation), in addition to the foregoing, include:

- D. A. Davies, "Anodic Voltammetric Determination of Monochloramine in Water" M. S. thesis, University of Wisconsin, Milwaukee, Wis., USA, 1985.
- A. N. Tsaousis, "Amperometric Determination of Hypochlorous Acid and Monochloramine at Gold Electrodes," M.S. thesis, University of Wisconsin, Milwaukee, Wis., USA, 1985
- B. Piela, P. K. Wrona, "Electrochemical Behavior of Chloramines on the Rotating Platinum and Gold Electrodes." *J. Electrochem. Soc.* 150 (5) (2003) 255-265.

SUMMARY OF THE INVENTION

Accordingly, an object of the present invention is to provide a chloramine sensor which is not subject to dissolved oxygen (DO) interference.

To achieve the foregoing objective, the present invention provides a solid state amperometric chloramine sensor/microsensor that uses an electrode response, i.e., current (pA) under a controlled applied potential (V) (amperometrically), for measuring monochloramine in aqueous solutions. The present invention uses gold (Au), platinum (Pt), carbon fiber, or carbon nanotube in compact form, as a sensing material (sensing element) to measure aqueous monochloramine concentrations.

The present invention provides a monochloramine microsensor which includes an elongated housing defining a central axis and an open interior and having a capillary opening at one end. A semi-permeable membrane covers the capillary opening, the semi-permeable membrane allowing diffusion of chloramines there-through while preventing water from entering into the interior of the housing. A chloramine sensitive element in the form of a wire, fiber or nanotube is mounted within the housing, the chloramine sensitive element, when used in conjunction with an anode, outputs current in an amount proportional to the concentration of chloramine present in a liquid sample in which the chloramine sensitive element is immersed. The chloramine sensitive element extends along a length of the central axis to a first end adjacent to and spaced from the semi-permeable membrane. The chloramine sensitive element is a gold wire, a platinum wire, a carbon fiber or a carbon nanotube. The capillary opening at the one end may suitably have an inner diameter of 5-10 microns and the first end of the chloramine sensitive element may suitably be spaced from the semi-permeable membrane by 5-6 microns. In a preferred embodiment the housing is a single piece construction with a section which is tapered to the capillary opening.

In another embodiment an anode, serving as a reference electrode, is mounted within the housing and the interior of the housing is at least partially filled with an electrolyte.

In contrast to the non-compact prior art electrodes mentioned above, the present invention provides a solid state amperometric chloramine sensor/microsensor in a compact form with a compact monochloramine sensing element in the compact form of a gold wire, platinum wire, carbon fiber or carbon nanotube. The compact sensing element enables fabrication of the needle-type (needle-like) chloramine sensor of the present invention which may be used for monochloramine measurement at a microscopic level which is impossible with the prior art sensors. Due to the needle-like (~10 microns) electrode design of the sensor of the present invention, the sensor is capable of penetrating very small microenvironments, e.g., pipe-scale, biofilm, or any other liquid-solid interface in natural or engineered aquatic systems, without destroying its structure. The microscale (needle-like) tip of the sensor of the present invention enables it to perform in situ measurement of chemical and biological species both spatially (<20 micron spatial resolution) and temporally, thus allowing the study of disinfectant diffusion, penetration, and related kinetics. With microprofiles and using the Monod growth model, the constituent flux (J) and the diffusion coefficient (D) at a given location in a floc or biofilm can be determined and kinetics in complex aqueous systems, e.g., biofilm and pipe-scale, can be analyzed. Thus, the present invention provides significant advantages over prior sensing technologies using macroelectrodes or lab-on-a-chip devices.

Another advantage of the present invention is that, unlike the prior art sensors, the sensor of the present invention does not require complex calibration curves such as the 3D surface shown in FIG. 5 to provide accurate monochloramine measurement, which requirement limits the use of the prior art sensors. On the contrary, the present invention can be operated under conditions where dissolved oxygen does not interfere with amperometric monochloramine measurements, expanding its applications and simplifying its implementation because only a single calibration curve, i.e., straight line, is required for a wide range of dissolved oxygen concentrations.

The monochloramine sensor of the present invention can be combined with molecular methodology and/or microscopic observation to determine inactivation and degradation kinetics of microbial biofilm cultures during disinfection and to evaluate biofilm control strategies/current operational responses to nitrification used by water utilities. The sensor of the present invention can also be combined with other microprocessors capable of probing biofilm for additional water parameters, e.g., free chlorine, ammonium, phosphate, oxidation-reduction potential, nitrate, nitrite, dissolved oxygen (DO), thus enabling water utilities to collect fundamental profile data to further develop nitrification control strategies to reduce nitrification episodes.

A primary utility of the present invention is use by drinking water utilities and drinking water distribution systems which use chloramines as disinfectant. This utility extends to any disinfection process using chloramines in water/wastewater treatment of biomedical disinfection, especially biofilm control.

More specifically, another utility of the present invention is real time monochloramine monitoring over a wide area in chloraminated drinking water distribution systems through integration with wireless smart grid technology. In addition, the present invention could be transformed to detect multiple analytes simultaneously with a single device, using microelectromechanical systems (MEMS) to incorporate different sensing techniques, e.g., potentiometry and amperometry, and different working electrodes.

DESCRIPTION OF THE PREFERRED EMBODIMENTS

Figure 1:
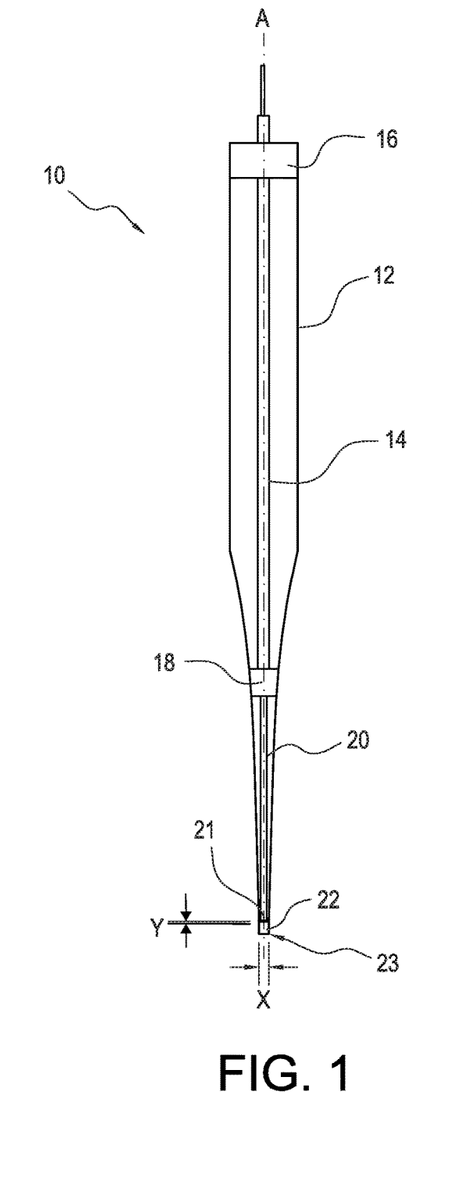
FIG. 1 is a schematic diagram of a first embodiment of the solid state amperometric chloramine microsensor of the present invention.

FIG. 1 shows a solid state amperometric sensor 10 which is an embodiment of the present invention which may be used in combination with a conventional Ag/AgCl reference electrode to measure the amount of chloramine in engineered or natural waters and aqueous solutions. The sensor 10 includes an elongated housing 12, in the form of a glass capillary, extending along a central axis A. The elongated housing 12 tapers to a capillary at the tip end 23 (lower end in FIG. 1). A conductive wire 14, for example a copper wire, extends through an upper seal 16 into the sealed interior space within the housing 12, along the central axis A, to a junction 18 within the housing 12. The upper seal 16 may be any conventional seal forming material such as glue or an elastomer, e.g., an epoxy rubber, as in the second embodiment shown in FIG. 2 and can have an internal diameter between 100 and 1500 microns, and preferably about 1100 microns.

A junction 18 within the housing 12 serves to electrically connect and bond the conductive wire 14 with a sensing element 20 which extends from the junction 18 to an end 21 slightly short of the capillary tip end 23 (lower end) of the housing 12. The inner diameter X of the open capillary tip end of the housing 12 is suitably 5-7 microns. It is appreciated that the inner diameter X of the open capillary tip end of the housing 12 can be between 1 to 100 microns. A semi-permeable membrane 22 covers and seals off the tip end 23 of the housing 12. The lower end 21 of the sensing element 20 is separated (recessed) from the semi-permeable membrane by a distance Y which is between 1 and 100 microns, but preferably 5-6 microns. The semi-permeable membrane 22 selectively allows the monochloramine to diffuse there-through from an aqueous solution sample and into contact with the lower end of the sensing element 20. Thus, Y defines a constant diffusive length for the monochloramine. The semi-permeable membrane also serves to protect the sensing element 20.

Suitable materials for the sensing element 20 include gold and platinum wires, carbon fibers and carbon nanotubes.

The junction 18 may be any material which has high electrical conductivity and strong conductive bonding. Examples of such a material include bismuth alloys and silver-filled epoxies.

The primary use of the chloramine sensor is in testing and/or monitoring engineered and natural aqueous solutions (e.g., chloraminated drinking water distribution systems or any chloramine system). Therefore, the general operating conditions for chloramine measurement are pHs between 6 and 9 and chlorine to nitrogen mass ratios ($Cl_2$:N) less than 5:1, resulting in the predominant chlorine species present being monochloramine. The applied potential for the monochloramine microsensor is a positive potential which does not result in dissolved oxygen interference.

Figure 2:
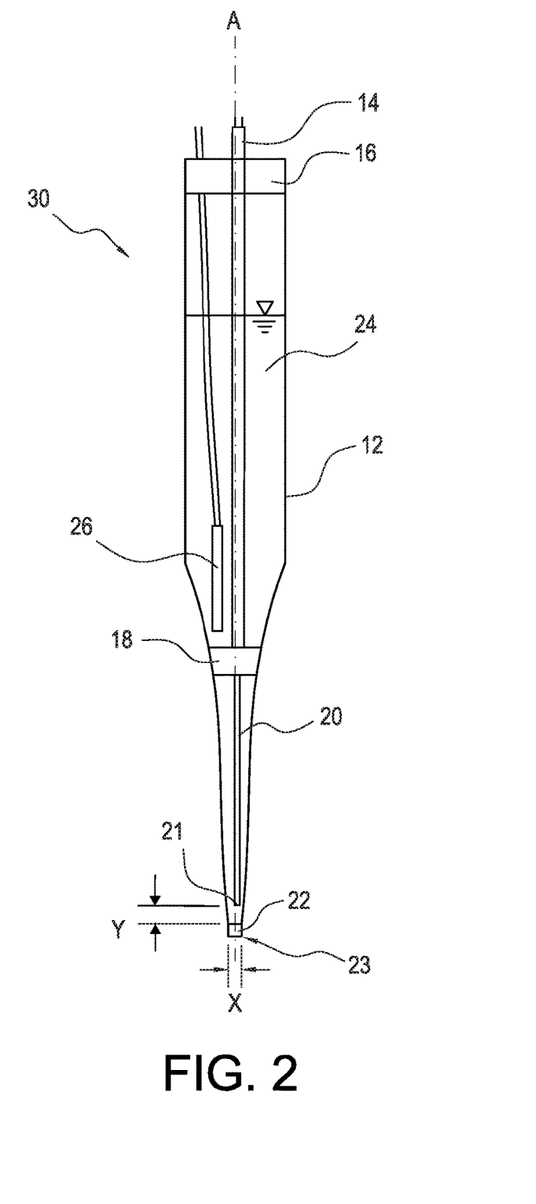
FIG. 2 is a schematic diagram of a second embodiment of the solid state amperometric chloramine microsensor of the present invention with an internal reference electrode.

FIG. 2 shows a second embodiment of the chloramine sensor of the present invention wherein a chloramine sensor 30 is provided with an internal reference electrode (e.g., Ag/AgCl reference electrode) 26. In this second embodiment the housing (outer casing) 12, in the form of a glass capillary, is at least partially filled with a suitable internal electrolyte 24. The reference electrode 26 used in testing by the present inventors was a 0.25 mm silver wire coated with AgCl and the internal electrolyte 24 was 0.1 M KCl+0.3 M $K_2CO_3$+0.2 M $KHCO_3$, pH 10.3. In the second embodiment the inner diameter of the capillary tip end is 7-10 microns, slightly larger than that of the first embodiment.

Figure 3:
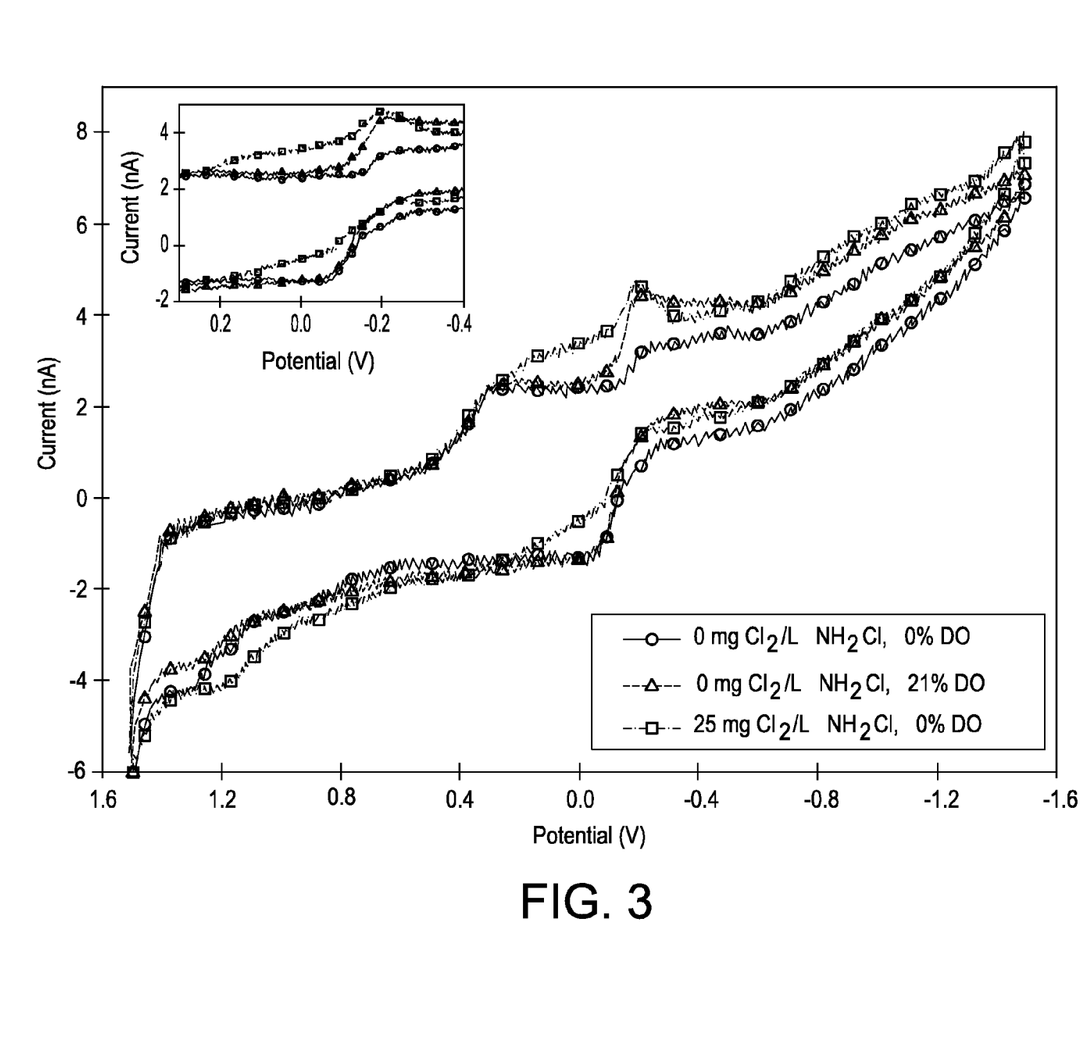
FIG. 3 shows a cyclic voltammogram (CV) for an embodiment of the solid state amperometric chloramine microsensor of the present invention wherein the sensing material is a gold wire.

FIG. 3 shows a cyclic voltammogram (CV) obtained using the first embodiment, i.e., FIG. 1, of the monochloramine sensor (~10 μm tip diameter) with a solid gold wire for various monochloramine and dissolved oxygen (DO) concentrations. With no monochloramine and between 0% and 21% DO, positive (+) potentials after approximately 0 V when scanned in the positive direction (FIG. 3) result in no changes in electrode response with changes in DO concentration, indicating a lack of DO sensitivity. After 25 mg $Cl_2$ $L^{-1}$ of monochloramine addition, the electrochemical oxidation and reduction of monochloramine were observed, indicating two ranges for potential monochloramine detection.

Starting at approximately +0.8 V, the electrochemical monochloramine oxidation (Eq. 1 and Eq. 2) proceeds by reaction with gold surface oxides as follows:

$$2Au+2OH^- \rightarrow 2AuOH+2e^- \qquad (Eq.\ 1)$$

$$2AuOH+2NH_2Cl \rightarrow N_2H_4+2HCl+O_2+2Au \qquad (Eq.\ 2)$$

However, as reported by A. N. Tsaousis, *Amperometric Determination of Hypochlorous Acid and Monochloramine at Gold Electrodes*. M.S. thesis, University of Wisconsin, Milwaukee, Wis., USA, (1985), gold surface oxide accumulation has been shown to lead to the loss of electrode activity, limiting its application for continuous monochloramine monitoring. Therefore, the monochloramine reduction reaction (Eq. 3), occurring between 0 and +0.25V, was chosen to measure monochloramine [3] without DO interference.

$$NH_2Cl+2H_2O+2e^- \rightarrow NH_4^+ + Cl^- + 2OH^- \qquad (Eq.\ 3)$$

FIG. 3 shows a cyclic voltammogram (CV) obtained with a microsensor 10 according to the first embodiment of the present invention having a gold wire as the sensing element 20, with the microsensor immersed together with a reference electrode in 5 mM pH 8.0 boric acid/sodium hydroxide (buffer) solution and 23° C. with different DO and monochloramine (4:1 $Cl_2$:N) concentrations. The scan was initiated at +1.5 V vs. Ag/AgCl in negative direction at 200 mV $s^{-1}$. The inset in FIG. 3 is a zoomed window showing between +0.3 V to −0.4 V of scanned potentials.

Figure 4:
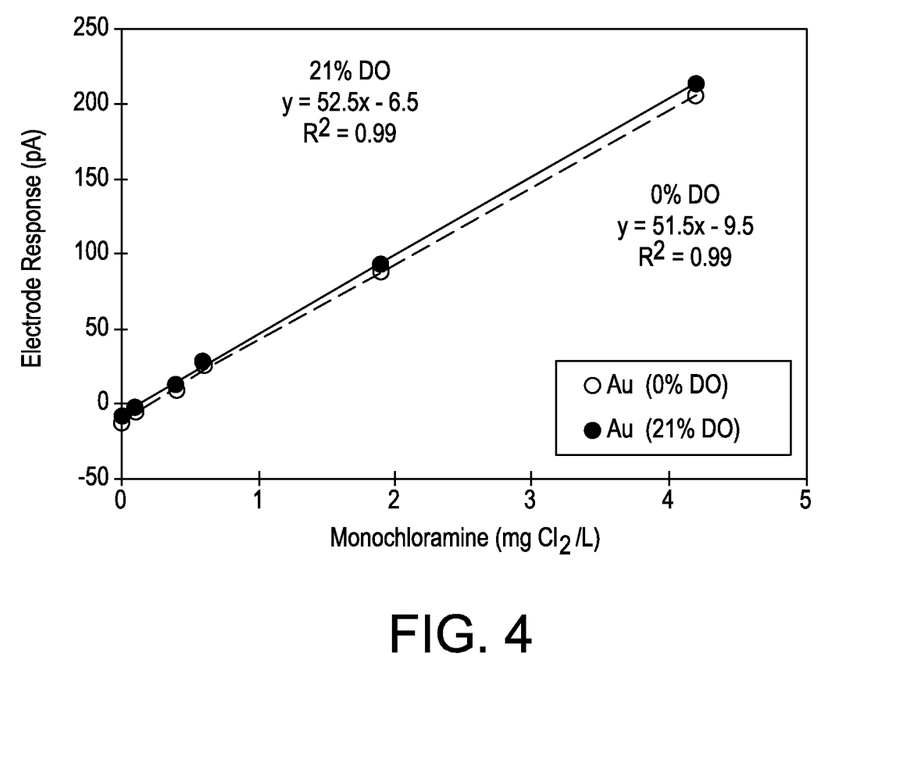
FIG. 4 is a representative monochloramine calibration curve for the first embodiment of the solid state amperometric chloramine microsensor of the present invention using gold wire as the sensing material.

FIG. 4 is a representative monochloramine calibration curve obtained with the first embodiment, i.e., FIG. 1, of the present invention having a gold wire as the sensing element 20 and using a 5 mM borate buffer solution, pH 8.0, 4:1 $Cl_2$:N ratio, and at 23° C. FIG. 4 shows that the gold microsensor of the present invention has an output that is linear with monochloramine concentration and is not subject to DO interference. The baseline signal (i.e., signal without monochloramine) is close to zero. The sensor 10 has a fast (<5 seconds), highly stable, and excellent amperometric electrode response to monochloramine over a wide concentration range (0-10 mg $Cl_2$ $L^{-1}$), including the primary range of interest (0-4.2 mg $Cl_2$ $L^{-1}$) with a sensitivity of at least 52±0.7 pA mg $Cl_2^{-1}$ L and a lower detection limit of at most 0.12±0.013 mg $Cl_2$ $L^{-1}$.

Figure 7:
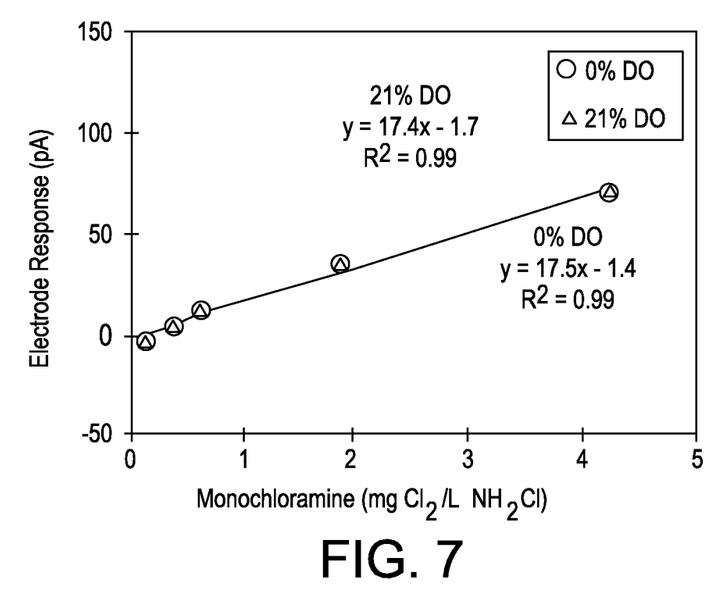
FIG. 7 is a representative monochloramine calibration curve of an embodiment of the solid state microsensor of the present invention wherein the sensing material is a platinum wire.

FIGS. 5-7 present a comparison of monochloramine calibration curves obtained using modifications of previous chloramine sensors, W. H. Lee et al (2011) and W. H. Lee et al (2010), FIGS. 5 and 6, respectively, and the present invention with a platinum wire, FIG. 7. The multiple calibration curves of FIGS. 5 and 6 result from DO interference, while the single calibration curve of FIG. 7 indicates lack of any DO interference for monochloramine measurement (using a 5 mM borate buffer solution, pH 8.0, 4:1 $Cl_2$:N ratio, and at 23° C.). The current invention using platinum wire has been optimized and, as shown in FIG. 7, does not exhibit oxygen interference.

Figure 8:
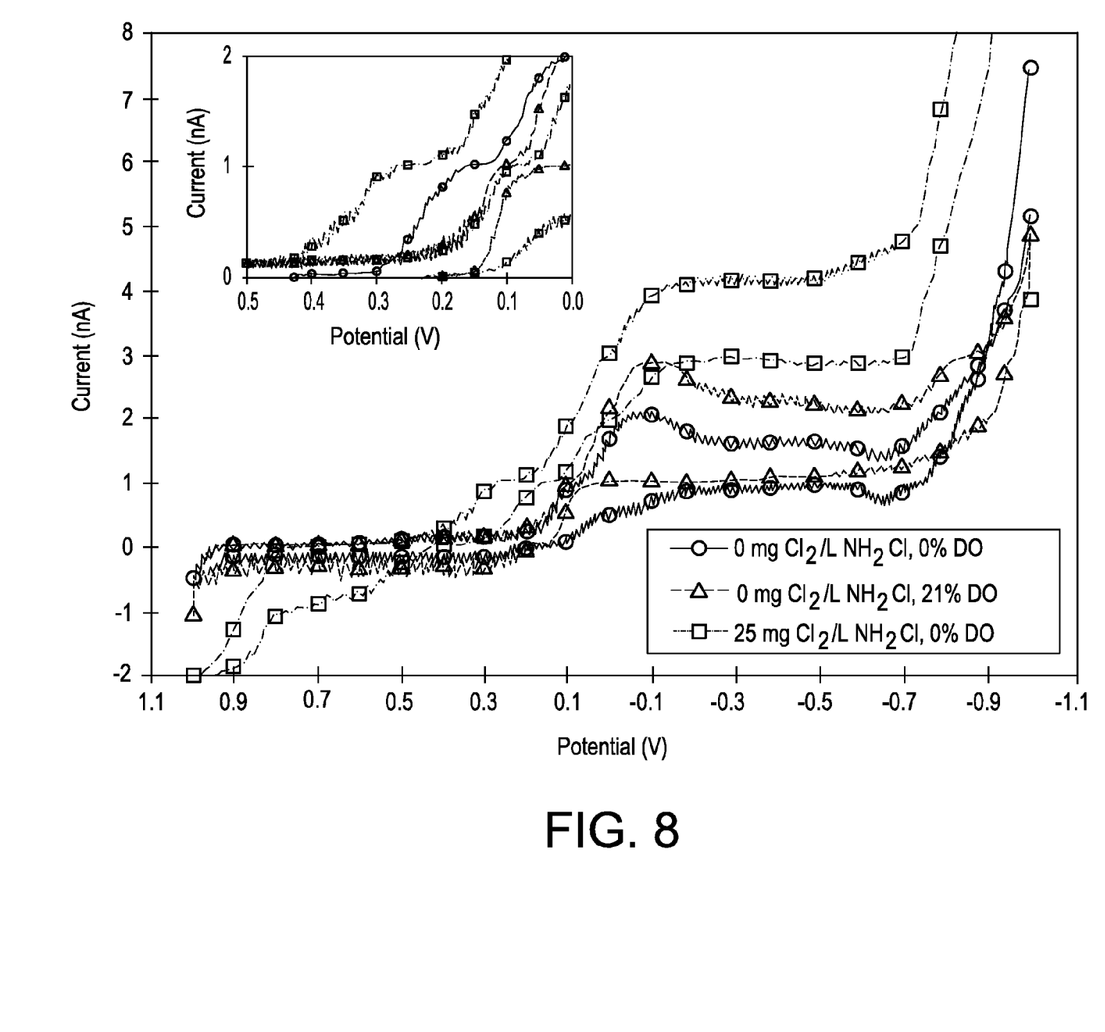
FIG. 8 is a cyclic voltammogram (CV) of an embodiment of the solid state microsensor of the present invention wherein the sensing material (element) is platinum.

FIG. 8 shows a cyclic voltammogram (CV) of platinum (Pt) microsensor immersed in a 5 mM pH 8.0 boric acid/sodium hydroxide (buffer) solution and 23° C. with different DO and monochloramine (4:1 $Cl_2$:N) concentrations. It represents a scan initiated at +1.5 V vs. Ag/AgCl in negative direction at 10 mV $s^{-1}$. Inset is a zoomed window between +0.5 V to 0.0 V of scanned potentials. FIG. 8 shows a representative platinum sensor CV of the invented monochloramine sensor (~10 μm tip diameter) with solid platinum wire. Similar to that seen with gold, the electrochemical oxidation and reduction of monochloramine were observed, indicating two ranges of potential monochloramine detection (FIG. 8). Starting at approximately +0.5 V, the electrochemical monochloramine oxidation (Eq. 4 and Eq. 5) has been shown to proceed where platinum oxides react with monochloramine. See D. A. Davies, M.S. thesis, University of Wisconsin "Anodic Voltammetric Determination of Monochloramine in Water," M.S. thesis, University of Wisconsin, Milwaukee, Wis., USA, 1985.

$$2Pt+2OH^- \rightarrow 2PtOH+2e^- \qquad (Eq.\ 4)$$

$$2PtOH+2NH_2Cl \rightarrow N_2H_4+2HCl+O_2+2Pt \qquad (Eq.\ 5)$$

Monochloramine reduction at platinum was observed at decreasing potentials from approximately +0.45 V with the same reaction (Eq. 3) as gold [3]; however, DO interference was observed with potentials lower than approximately +0.15 V. Consequently, any potential between +0.15 and +0.45 V may be used as the applied potential, resulting in no DO interference while producing a highly stable electrode response to monochloramine. The monochloramine concentration is determined from the measured current using a calibration curve (FIG. 7).

The present invention may be embodied in other forms without departing from the spirit and scope of the appended claims. The foregoing embodiments are intended to be illustrative only and do not limit the scope of the appended claims.

We claim:

1. A microsensor for quantitative analysis of chloramines in aqueous systems, comprising:
    an elongated housing defining a central axis and an open interior and having a capillary opening at one end;
    a semi-permeable membrane covering the capillary opening, the semi-permeable membrane allowing diffusion of chloramines there-through while preventing water from entering into the open interior of the elongated housing;
    a chloramine sensitive element in a form of a wire, fiber or nanotube mounted within the elongated housing, the chloramine sensitive element, when used in conjunction with an anode, outputting current in an amount proportional to a concentration of chloramine present in a liquid sample in which the chloramine sensitive element is immersed, the chloramine sensitive element extending along a length of the central axis to a first end adjacent to and spaced at a constant diffusive length from the semi-permeable membrane.

2. The microsensor of claim 1 wherein the chloramine sensitive element is a gold wire, a platinum wire, a carbon fiber or a carbon nanotube.

3. The microsensor of claim 1 wherein the capillary opening at the one end has an inner diameter of 5-10 microns.

4. The microsensor of claim 1 wherein the first end of the chloramine sensitive element is spaced from the semi-permeable membrane by 5-6 microns.

5. The microsensor of claim 1 wherein the elongated housing includes a section which is tapered to the capillary opening.

6. The microsensor of claim 1 additionally comprising an anode, serving as a reference electrode, mounted within the elongated housing, wherein the open interior of the elongated housing is at least partially filled with an electrolyte.

7. The microsensor of claim 6 additionally comprising a conductive wire extending within the elongated housing over a length of the elongated housing and joined at a junction to a second end of the chloramine sensitive element.

8. The microsensor of claim 7 wherein the junction is a material which is electrically conductive and provides strong bonding of the conductive wire to the chloramine sensitive element.

9. The microsensor of claim 6 additionally comprising a seal closing a second end, opposite the one end, of the elongated housing.

10. The microsensor of claim 1 additionally comprising a conductive wire extending within the elongated housing over a length of the elongated housing and joined at a junction to a second end of the chloramine sensitive element.

11. The microsensor of claim 10 wherein the junction is a material which is electrically conductive and provides strong bonding of the conductive wire to the chloramine sensitive element.

12. The microsensor of claim 1 additionally comprising a seal closing a second end, opposite the one end, of the elongated housing.

13. A microsensor for quantitative analysis of chloramines in aqueous systems, comprising:
    an elongated housing defining a central axis and an open interior and having a capillary opening at one end;
    a semi-permeable membrane covering the capillary opening, the semi-permeable membrane allowing diffusion of chloramines there-through while preventing water from entering into the open interior of the elongated housing;
    a compact chloramine sensitive element in a form of a wire, fiber or nanotube mounted within the elongated housing, the compact chloramine sensitive element, when used in conjunction with an anode, outputting current in an amount proportional to a concentration of chloramine present in a liquid sample in which the compact chloramine sensitive element is immersed, the compact chloramine sensitive element extending along a length of the central axis to a first end adjacent to and spaced at a constant diffusive length from the semi-permeable membrane.

14. The microsensor of claim 1, wherein the microsensor is configured in a way such that the microsensor lacks dissolved oxygen sensitivity.

15. The microsensor of claim 1, wherein the microsensor is configured in a way such that the microsensor is operable with a positive applied potential.

16. The microsensor of claim 15, wherein the positive applied potential is between 0.15 and 0.45 V.

17. The microsensor of claim 15, wherein the positive applied potential is between 0 and 0.25 V.

18. A process for quantitative analysis of chloramines in aqueous systems, comprising the use of the microsensor of claim 1 with a reference electrode in a 5 mM pH 8.0 boric acid/sodium hydroxide buffer solution at a temperature of 23° C. with different DO and monochloramine (4:1 $Cl_2$:N) concentrations, wherein said chloramine sensitive element comprises a gold wire.

19. A process for quantitative analysis of chloramines in aqueous systems, comprising the use of the microsensor of claim 1 with a reference electrode in a 5 mM pH 8.0 boric acid/sodium hydroxide buffer solution at a temperature of 23° C. with different DO and monochloramine (4:1 Cl2:N) concentrations, wherein said chloramine sensitive element comprises a platinum wire.

20. The process of claim 19 wherein a potential between +0.15 and +0.45 V is applied.

* * * * *